United States Patent [19]

Miyoshi et al.

[11] Patent Number: 4,520,341
[45] Date of Patent: May 28, 1985

[54] MOISTURE RESPONSIVE ELEMENT WITH CROSSLINKED ORGANIC MEMBRANE AND PROTECTIVE LAYERING

[75] Inventors: Shuji Miyoshi, Osaka; Takashi Sugihara, Tenri; Akihito Jinda, Nara; Masaya Hijikigawa, Yamatokouriyama, all of Japan

[73] Assignee: Sharp Kabushiki Kaisha, Osaka, Japan

[21] Appl. No.: 446,405

[22] Filed: Dec. 2, 1982

[30] Foreign Application Priority Data

Dec. 8, 1981 [JP] Japan ............................ 56-198027
Apr. 14, 1982 [JP] Japan ............................ 57-62791

[51] Int. Cl.³ .................. H01C 3/00; G01N 27/12; H01C 7/00
[52] U.S. Cl. ........................... 338/35; 73/335; 73/336.5
[58] Field of Search ............. 338/34, 35; 324/65 R, 324/65 P; 73/336.5, 335, 29, 336; 422/98

[56] References Cited

U.S. PATENT DOCUMENTS 2,728,831 12/1955 Pope .................... 73/336.5
3,671,913 6/1972 Mamiya et al. ............... 338/35
3,848,218 11/1974 Wakabayashi et al. .......... 338/35
3,983,527 9/1976 Ohsato et al. ................ 338/35
4,040,984 8/1977 Sharpe et al. ............. 524/901 X
4,163,384 8/1979 Blakemore ................... 73/29
4,167,725 9/1979 Shimizu et al. ............... 338/35

FOREIGN PATENT DOCUMENTS 7190258 5/1981 Japan ....................... 324/65 R
199709 9/1977 U.S.S.R. ..................... 338/34

Primary Examiner—Roy N. Envall, Jr.
Assistant Examiner—C. N. Sears
Attorney, Agent, or Firm—Birch, Stewart, Kolasch & Birch

[57] ABSTRACT

A moisture responsive element comprises a moisture responsive organic membrane in contact with electrically conductive members, in which the organic membrane consists essentially of a crosslinked organic polymer having a hydrophilic group. The element has excellent water and moisture resistance, long-term stability and excellent humidity response over a range of humidity from 0 to 100 percent. The moisture responsive element includes a protective layer of cellulose acetate and/or polyvinyl acetate.

7 Claims, 6 Drawing Figures

MOISTURE RESPONSIVE ELEMENT WITH CROSSLINKED ORGANIC MEMBRANE AND PROTECTIVE LAYERING

BACKGROUND OF THE INVENTION

In moisture-responsive elements which change in electrical resistance or electrical capacity in response to ambient moisture or vapor, the following materials have been used:

(1) Sintered metal oxide membranes such as iron oxides ($Fe_2O_3$ or $Fe_3O_4$), tin oxides ($SnO_2$) and the like;
(2) Electrolytes such as lithium chloride (LiCl);
(3) Dispersions of electrically conductive particles or fibers in hygroscopic resin or polymer membrane;
(4) Temperature-sensing elements such as thermistors; and
(5) hydrophilic polymer membranes or polymeric electrolytes.

In general, the moisture responsive elements consisting of the metal oxides suffer from drawbacks, for example, a high electrical resistance which is considerably dependent on temperature, despite their excellent heat resistance and rapid moisture-responsive property. Particularly, the moisture responsive property of sintered metal oxides is not easily reproducible, and such elements are not easily interchanged, because the moisture responsive property is dependent on factors such as particle size, density of the sintered metal oxides and the like.

The moisture responsive elements consisting of electrolytes such as lithium chloride have only a narrow range of operation, so that two or more different kinds of moisture responsive elements are required in order to detect relative humidity over a broad range of, for example, from 0 to 100 percent, i.e. the whole humidity range. Further, there is a problem related to the useful life time of the electrolyte moisture responsive element. When held under a high moisture condition, i.e under a relative humidity of more than 90 percent, the electrolyte is leached or diluted and the moisture responsive property is considerably deteriorated.

The moisture responsive elements made by dispersing electrically conductive particles or fibers in moisture absorbable resin are sensitive and change their electrical resistances in high moisture circumstances, but are not sensitive in low moisture circumstances. Therefore, such moisture responsive elements are not suitable to detect humidity over a wide range and are mainly used for detection of dropwise condensation.

The moisture responsive elements using temperature-sensing elements such as thermistors detect ambient humidity in response to the change of heat conductivity of gas or air in concert with the humidity therein. Therefore, these elements can be used to determine an absolute humidity, but are liable to be affected by ambient temperature and wind.

Moisture responsive elements with hydrophilic polymer membranes or electrolyte polymer membranes have been known. These are responsive to moisture over a wide range with sensitivity. Further, as the element has a simple structure and is comparatively easily produced, the cost for production can be minimized. However, such elements using polymer membranes have poor moisture or water resistance and a short life time, which is a very serious problem.

The problems in the moisture responsive elements as immediately aforementioned are caused by deficient water or moisture resistance of the moisture responsive membrane. That is, a conventional hydrophilic polymer membrane or electrolyte polymer membrane is dissolved or deteriorated, though slowly, under a high humidity condition i.e. a relative humidity of more than 90 percent, so as to lose its moisture responsive property. Particularly, when dewdrops are condensed on the surface of the moisture responsive membrane or the membrane is soaked in water, the membrane is rapidly dissolved to substantially lose its moisture responsive property.

SUMMARY OF THE INVENTION

In accordance with the present invention, a moisture responsive element comprises a substrate, a pair of electrically conductive members, and a moisture responsive organic membrane, in which the electrically conductive members are separated from each other and held between the substrate and the moisture responsive organic membrane, characterized in that the organic membrane consists essentially of a crosslinked organic polymer having a hydrophilic group. A method for producing the element is provided.

The moisture responsive element has excellent water and moisture resistance and stability for a long time and has an excellent humidity responsive property over a wide range of humidity such as from 0 to 100 percent.

Further, according to the present invention, a moisture responsive element comprises a substrate, a pair of electrically conductive members, a moisture responsive organic membrane and a protective layer, in which the electrically conductive members are separated from each other and held between the substrate and the moisture responsive organic membrane, and the moisture responsive organic membrane is covered with the protective layer characterized in that the organic membrane consists essentially of a crosslinked organic polymer having a hydrophilic group and the protective layer consists essentially of cellulose acetate and/or polyvinyl acetate. Deterioration of the moisture responsive property of the element from pollutants such as oil dust, nicotine from cigarettes and the like is prevented.

As aforementioned, the conventional moisture responsive element consisting of polymer membrane has many defects such as poor water and moisture resistances and a short life time. It has been found that the defects are attributed to a high water solubility of the conventional membrane. If a non-soluble vapor impermeable is coated on the surface of the moisture responsive membrane, the above problems may be solved to a certain degree, but the moisture responsive rate of the element will decrease.

The essential principle of actuation of the above membrane type moisture responsive element is the variation of impedance between electrodes caused by change in electrical conductivity of protons, anions or cations in the membrane due to absorption and desorption of water molecules in the humidity responsive membrane. Therefore, in order to respond to a wide humidity range, it is desirable that the moisture responsive membrane be made from a membrane which is hydrophilic yet easily absorbs and desorbs water. Also, in order to provide water and moisture resistance, it is required that the humidity responsive membrane be hardly soluble in water and free from deterioration under high humidity circumstances. These requirements are inconsistent with each other. However, it is necessary to resolve the inconsistency in order to obtain humidity responsiveness and a sufficiently long life time.

In accordance with the present invention a moisture responsive element comprises a substrate, a pair of electrically conductive members and a moisture responsive organic membrane, in which the electrically conductive members are spaced from each other on the substrate and held between the substrate and the organic membrane, characterized in that the organic membrane consists of a crosslinked organic polymer having a hydrophilic group. A method for producing such a moisture responsive element is provided.

DETAILED DESCRIPTION

Figure 1:
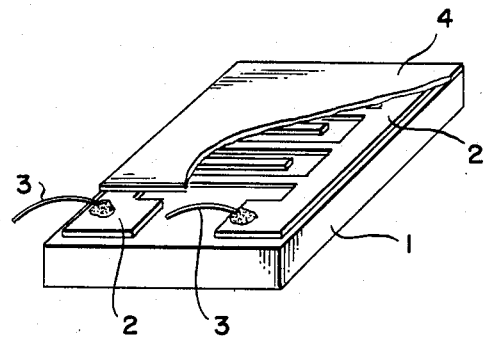
FIG. 1 is a partially cut-away perspective view of a first embodiment of the present invention.

An embodiment of the moisture responsive element of the present invention is illustrated in FIG. 1.

As shown in FIG. 1, two conductive members (2) are adhered on one surface of the substrate (1) and are separated from each other to form a pair of electrodes which are connected to wires (3) respectively. The surface of the substrate on which the electrically conductive members are placed is coated by a continuous polymer membrane (4) in such manner that the electrically conductive members are held between the substrate and the polymer membrane.

The substrate (1) may be a conventional one having high electrical insulation, for example, alumina, glass, sapphire and the like.

Electrically conductive members (2) may also be conventional, for example, copper, gold, platinum, ruthenium oxide and the like. The electrically conductive members may be adhered on the surface of the substrate by any conventional method, though most preferably by high-vacuum metal deposition or spattering. The electrically conductive members may be comb-shaped. Further, the comb-shaped electrically conductive members preferably are placed in such manner that the teeth of the respective combs alternate with each other.

The impedance of the moisture responsive organic membrane of the present invention varies in response to humidity. The membrane has a hydrophilic residue in the polymer molecular.

Preferable hydrophilic groups are sulfonic acid group, carbonyl group, hydroxyl group, amono group and the like. Sulfonic acid or the salts thereof are most preferable.

The sulfonic acid group may be formed after polymerization. For instance, monomer having no hydrophilic group such as styrene is polymerized with a crosslinking agent on the electrically conductive material to form a polymer membrane on the surface, and then the obtained polymer membrane is treated with sulfonic acid.

Preferable monomers having hydrophilic group are styrene sulfonic acid, methylstylene sulfonic acid, 2-acrylamide-2-methylpropane sulfonic acid and the like and the salts thereof, most preferably, styrene sulfonic acid and the salt thereof.

Alkaline forming the salt of the hydrophilic group according to the present invention includes alkaline metals such as sodium, potassium, lithium and the like; alkaline earth metals such as magnesium, strontium, calcium and the like; ammonia; amines such as mono, di, and triamines having a lower alkyl group, polyalkyleneamines such as triethylenediamine, hexamethylenetetramine and the like; alkanolamines such as monoethanolamine, triethanolamine and the like; alkylalkanolamines such as monomethyldiethanolamine; urea; tetramethylguanidine and the like.

These monomers may be copolymerized with each other or with other monomers not containing hydrophilic groups such as styrene, butadien, acrylonitrile and the like, within 90 percent by weight of the total amount of the monomers.

Further, the organic polymer suitable for the membrane of the present invention has a crosslinkage. If the organic polymer has no crosslinkage, the moisture responsive properties are deteriorated under high humidity conditions as aforementioned. Preferably, a three dimensional crosslinked molecular structure is used for the membrane without deterioration of the hydrophilic property.

The crosslinking agent of the present invention has at least two reactive groups to monomers, preferably two reactive groups such as ethylenically double bonds, isocyanate group, and the like.

Examples of the crosslinking agents are N,N'-methylene-bis-acrylamide, divinylbenzene, hexatrien, divinyl sulfone, diallyl phthalate and the like. Most preferable crosslinking agents are N,N'-methylene-bis-acrylamide, divinylbenzene, hexatriene and the like.

The crosslinking agent may be used in a mole ratio (crosslinking agent/monomer) of from 0.01 to 0.2, preferably 0.06 to 0.1. If the amount of the crosslinking agent exceeds the mole ratio of 0.2, the obtained membrane becomes crackable by imbibition at absorption of moisture whereas the less than 0.01, durability to moisture becomes imperfect.

The crosslinked organic polymer having a hydrophilic group of the present invention may be obtained by the crosslinking of an organic polymer having a hydrophilic group with a crosslinking agent or by the in situ polymerization of monomers with the crosslinking agent on the electrically conductive material to form the polymer. The latter method is most preferable.

In another aspect, the present invention provides a moisture responsive membrane furnished with a protective layer.

As aforementioned, the moisture responsive element comprising an organic membrane is improved in moisture and water resistance by the crosslinking of the membrane. However, even such an improved membrane is defenseless to oily dust such as oily smoke, nicotine from cigarettes and so on. Particularly, a moisture responsive element having an organic membrane cannot be heated to a high temperature, for instance, 300° C. to 400° C., to burn up the oily dust deposited on the surface of the element as with an element comprising metal oxides. Therefore, the moisture responsive property of the element of the above first embodiment is deteriorated when polluted by the oily dust.

In accordance with another aspect of the present invention, a moisture responsive element comprises a substrate, a pair of electrically conductive members, a moisture responsive organic membrane and a protective layer, in which the electrically conductive members are separated from each other and held between the substrate and the moisture responsive organic membrane, and the moisture responsive organic membrane is covered by the protective layer characterized in that the organic membrane consists essentially of a crosslinked organic polymer having a hydrophilic group and the protective layer consists essentially of cellulose acetate and/or polyvinyl acetate.

Figure 4:
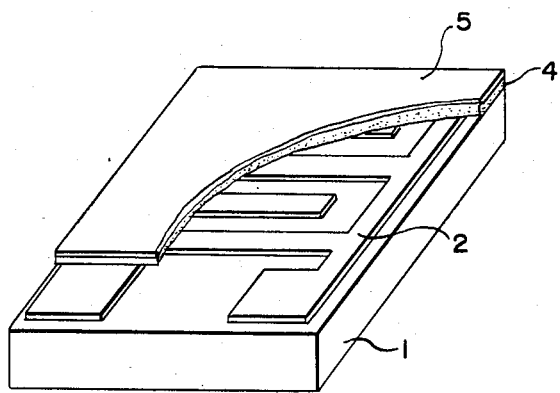
FIG. 4 is a partially cut-away perspective view of a second embodiment of the present invention.

The structure of the moisture responsive element of the second embodiment of the present invention is illustrated by FIG. 4. As apparent from FIG. 4, the element of the second embodiment has a protective layer (5) on the surface of the moisture responsive element of the first embodiment. The structure and materials of the substrate (1), the electrically conductive members (2), and the organic membrane (3) are as disclosed with respect to the first embodiment.

The protective layer (5) includes cellulose acetate and/or polyvinyl acetate, which may be used alone or together with another polymer having a relatively small hydrophilic property such as silicone resin, epoxy resin, urea resin, nylon and the like. When mixed with another polymer, the amount of the other polymer should be not more than 10 percent by weight based on the total amount of polymer of the protective layer.

The thickness of the protective layer is controlled, preferably from 0.5 μm to 10 μm.

The protective layer may be formed by a conventional method, for example, the element of the first embodiment may be soaked in solution of the above polymer in a proper solvent such as acetone. Spraying, brushing or rolling are also suitable.

Illustrating the inventions are the following examples which, however, are not to be construed as limiting the invention to their details. All parts and percentages in the examples as well as throughout this specification are by weight unless otherwise indicated.

EXAMPLE 1

An aqueous solution containing sodium styrene sulfonate (referred to as SSNa hereinafter), N,N′-methylene-bis-acrylamide (referred to as MBA) as a crosslinking agent and polyvinyl alcohol (referred to as PVA) in the ratio of 100:5:40 is coated on the surface of alumina board on which a pair of electrodes are patterned in the form of the teeth of combs, followed by the irradiation with ultraviolet rays to form a moisture responsive membrane.

The essential reaction processes of the forming of the moisture responsive membrane are as follows:

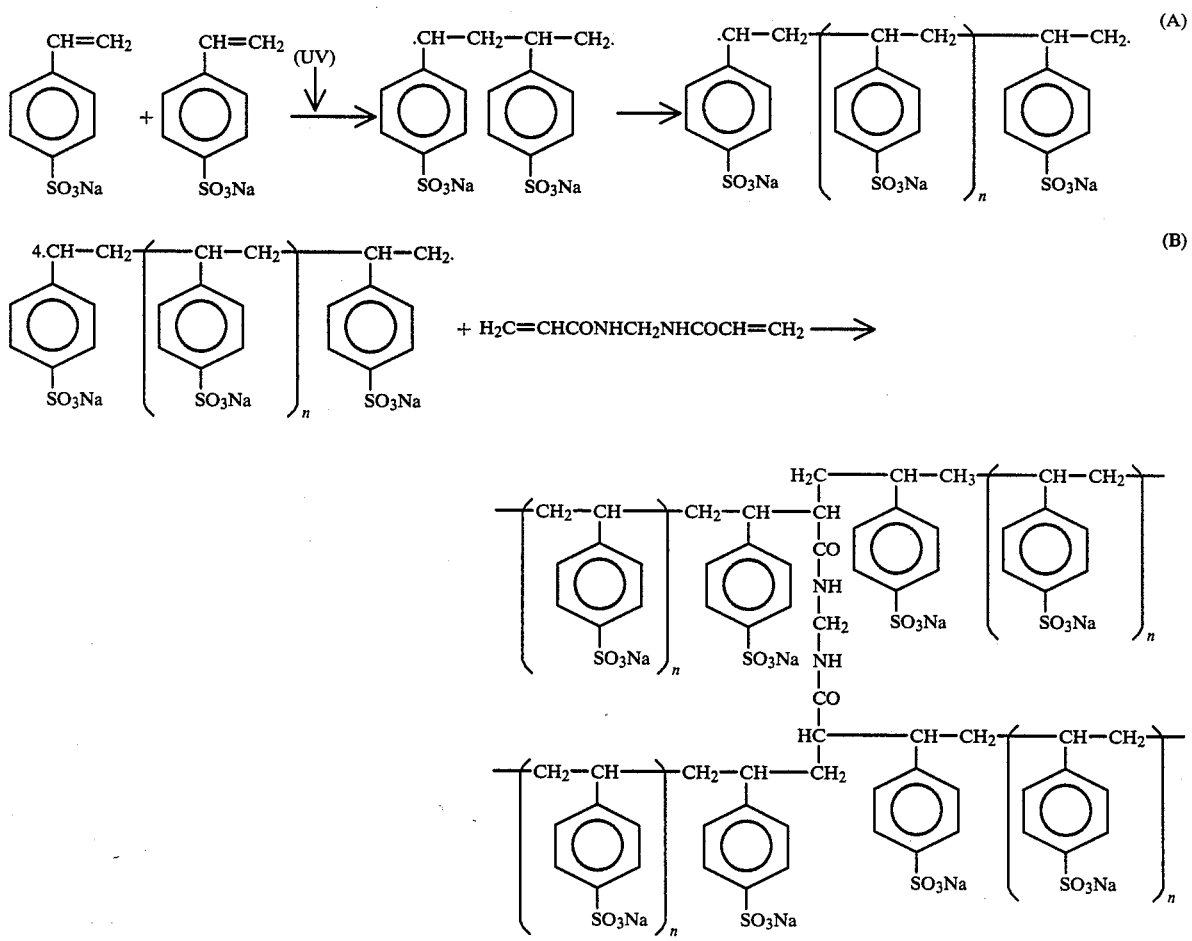

SSNa is polymerized by the radiation of the ultraviolet rays (referred to as UV hereinafter) to form sodium polystyrene sulfonate (referred to as PSS hereinafter)

according to the above process (A) with the crosslinkage of PSS by MBA as illustrated by the above process (B). As the result of the above reactions, a membrane consisting of PSS polymer chains crosslinked by MBA is finally obtained.

As aforementioned, such a moisture responsive membrane, in which the polymer chains are three dimensionally crosslinked is excellent in moisture and water resistance.

The moisture and water resistance of the obtained membrane is determined by soaking the membrane in water, which is the most severe test for determination of the moisture and water resistance. The result is shown in FIG. 2.

Figure 2:
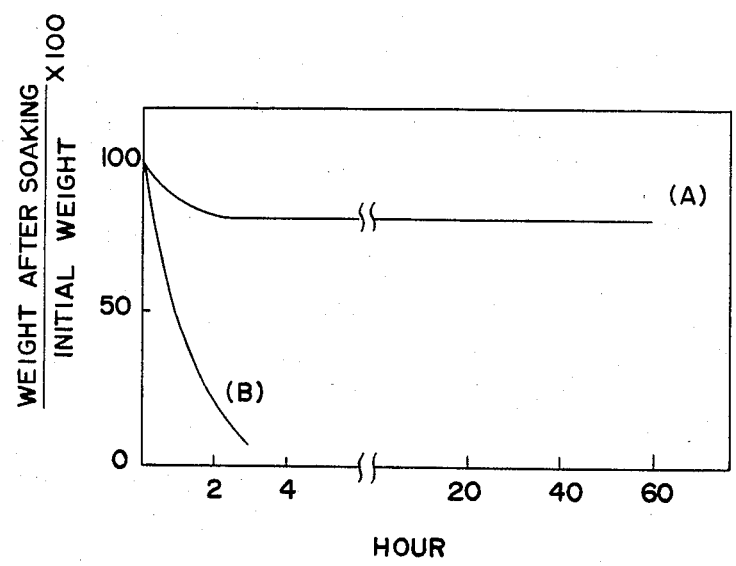
FIG. 2 is a graph indicating the relationship of a ratio of increase in the weight of a membrane to soaking time.
Figure 3:
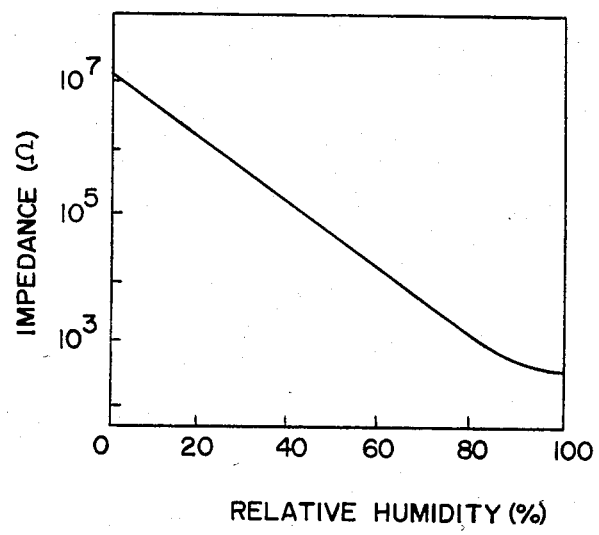
FIG. 3 is a graph showing the relationship of impedance to relative humidity.

In FIG. 2, Plot A shows the variation of percentage of weight of the inventive membrane leached into water as a function of time, which is determined by soaking for a given time, and drying and weighting the above membrance. As apparent from FIG. 2, initially a slight change of weight is observed. However, subsequent thereto, no more change is observed, which indicates that the property of the membrane is neither changed nor deteriorated. Further, the moisture responsive property of the membrane varies in a similar manner. That is, a slight increase of impedance is initially observed, but impedance remains stable after that. It is assumed that the initial decrease of the membrane in weight is caused by the leaching of some unreacted monomer in the membrane.

In FIG. 2, Plot B indicates the variation in weight of a membrane produced in the same way as Example 1 but without crosslinking agent, when the membrane is soaked in water. In this case, the membrane is completely dissolved within a short time. This difference from Example 1 is due to the absence of the crosslinking agent, and demonstrates that the crosslinking of the moisture responsive membrane is very important for the effectiveness and durability of a moisture responsive element made of organic polymer.

Figure 5:
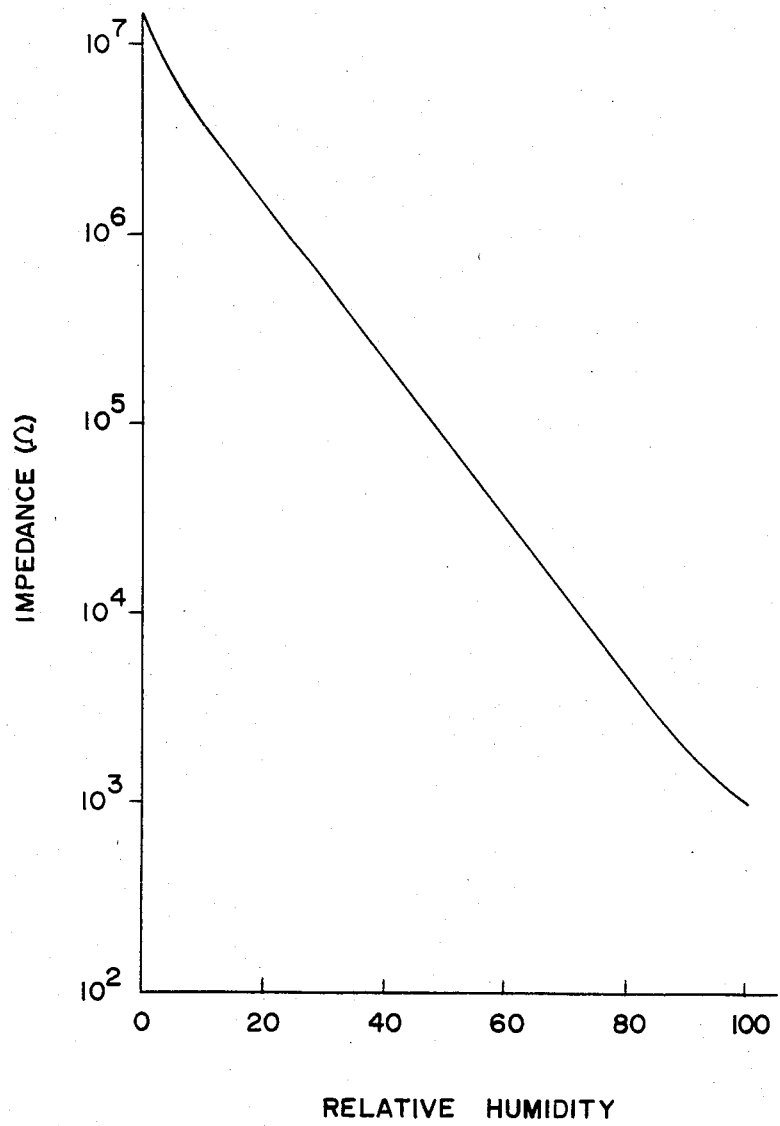
FIG. 5 is a graph indicating the relationship of impedance to relative humidity.

FIG. 5 illustrates a moisture responsive property (impedance-relative humidity property) of a moisture responsive element produced according to Example 1. The impedance of the element is detected via the comb-shaped electrodes and changes as a nearly exponential function over the whole relative humidity range of 0 percent to 100 percent. The moisture responsive property does not change even if the element is soaked in water or held at high humidity.

EXAMPLE 2

The solution of SSNa, divinylbenzene and PVA in the ratio of 100:40:40 respectively in dimethyl sulfoxide is coated on the surface of the substrate to form a moisture responsive membrane in the same manner as Example 1 to make a moisture responsive element. In this example, since PSS molecules are sufficiently crosslinked by divinylbenzene, the obtained membrane is not leached in water, and the moisture responsive property does not change in water or high moisture circumstances for a long time. Further, similar to the result of Example 1, the moisture responsive property changes as a nearly exponential function over a relative humidity range of 0 percent to 100 percent.

EXAMPLE 3

Using the solution of ammonium styrene sulfonate, MBA (crosslinking agent) and PVA at the ratio of 100:5:40 respectively in dimethyl sulfoxide, a moisture responsive element is produced in the manner of Example 1. The obtained element gives excellent results as in the above Examples.

In the above Examples, sodium styrene sulfonate and ammonium styrene sulfonate are used. However, styrene sulfonic acid or other salts thereof such as lithium salt, sodium salt, potassium salt, urea salt, triethylenediamine salt, tetramethylguanidine salt, hexamethylenetetramine salt and the like may also be used to obtain similar results.

Other crosslinking agents not disclosed in the above Examples may be used. For example, hexatriene, divinyl sulfone, and diallylphtharate give excellent results as in the above Examples.

Though the polymerization is initiated by the UV radiation in the above Examples, other conventional methods for the polymerization such as heating, irradiation or an initiator such as ammonium persulfate may be used.

In the present invention, as disclosed in Example 3, another non-crosslinked polymer such as polyvinyl alcohol may be combined with the crosslinked polymer for the control of the moisture responsive property of the membrane and of the viscosity of the solution. For this object, useful non-crosslinked polymers include polyvinyl alcohol, methyl cellulose and the like.

EXAMPLE 4

This example illustrates the second embodiment of the present invention including the moisture responsive membrane covered by another organic polymeric membrane, as illustrated in FIG. 4.

The moisture responsive element obtained in Example 1 is dipped into an acetate solution of cellulose acetate and dried to form a coated film on the surface of the element of Example 1. The obtained element is referred to as Element C. The moisture responsive property of Element C immediately after the preparation thereof is shown in FIG. 5. The element of Example 1 itself, i.e. an element having no cellulose acetate film layer, is referred to as Element D. Elements C and D each have nearly the same initial moisture responsive property as shown in FIG. 5.

The Elements C and D are hung within a cylindrical vessel having venting holes at the top and the bottom (a volume of about 500 ml). Oil vapor, nicotine of cigarette and smoke of a mosquito repellent spray are introduced intermittently to fill the vessel with these oily dusts.

Figure 6:
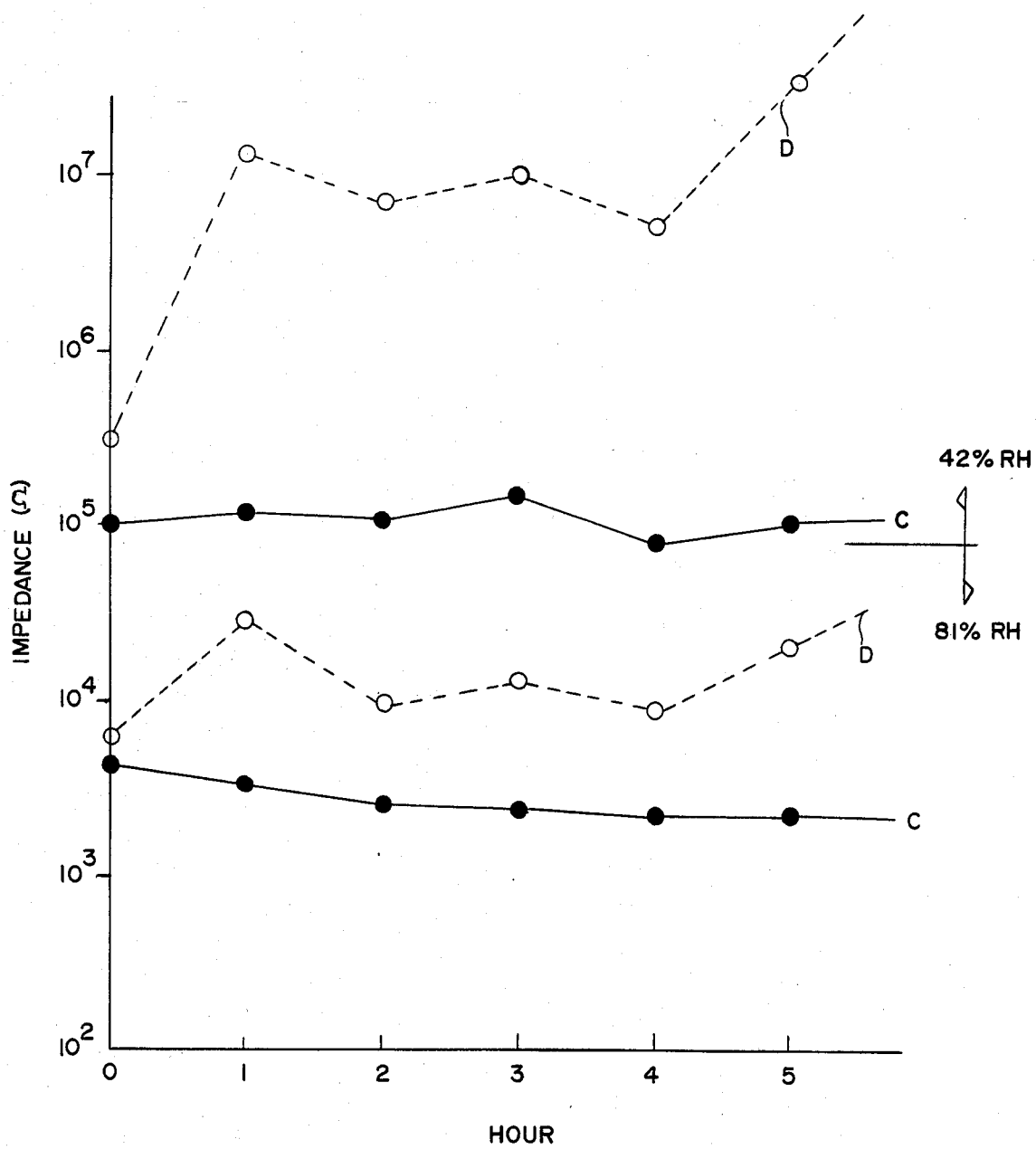
FIG. 6 is a graph indicating the relationship of impedance to time.

The moisture responsive properties of these elements are determined at intervals to estimate stain resistance to oily dust. FIG. 6 illustrates the variation of impedance of each element upon the introduction of the mosquito repellent spray as the only dust. In the FIG. 6, Plots C and D correspond to the Elements C and D respectively, and the relations between impedance and test time at relative humidities of 42 percent and 81 percent are illustrated.

Element C coated with cellulose acetate shows little variation at both low humidity (42%) and high humidity (81%), whereas Element D shows a remarkable increase in impedance at low humidity. The same results are obtained with oil vapor or the nicotine of cigarettes.

After treated about five hours with the oily dusts, the surfaces of Elements C and D indicate remarkable differences under a microscope. On the surface of the Element C, oil and nicotine are deposited in the form of separate small particles, whereas on the surface of Element D these oily dusts are spread as a considerably thick membrane. It is assumed that Element C maintains the initial moisture responsive property without an inhibition of moisture permeability of the moisture responsive membrane because of the manner of particle deposition of the oily dust. On the contrary, Element D is deteriorated in its moisture responsive property at the low humidity, because the moisture permeability of the moisture responsive membrane is lowered by the thick coating of the oily dust.

The same effect as from the above cellulose acetate is also achieved by polyvinyl acetate or a mixture of cellulose acetate and vinyl acetate.

These protective layers may be applied to other conventional moisture responsive elements, for example, metal oxides such as titanium oxide, alumina, tin oxide; semiconductors such as selenium and germanium; and other non-crosslinked organic membranes such as polystyrene sulfonic acid and the salt thereof. Such application of the cellulose acetate and/or polyvinyl acetate protects the moisture responsive element from the oily stain with thick membranes to give a long life time without deterioration of moisture responsive property.

What is claimed is:

1. A moisture responsive element consisting essentially of:
   an electrically non-conductive base plate;
   a pair of spaced electrodes fixed on said base plate;
   a moisture responsive organic membrane comprising an organic monomer and crosslinking agent consisting essentially of material selected from the group consisting of crosslinked polystyrene sulfonic acid and salt of polystyrene sulfonic acid extending over said pair of electrodes; and
   a protective layer consisting essentially of material selected from the group consisting of cellulose acetate and polyvinyl acetate coated on said moisture responsive organic membrane.

2. The moisture responsive element of claim 1, in which the crosslinking agent is selected from the group consisting of N,N'-methylene-bis-acrylamide, divinylbenzene, hexatriene, divinyl sulfone, and diallylphthalete.

3. The moisture responsive element of claim 1, in which a molar ratio of organic monomer to crosslinking agent is from 0.01 to 0.2.

4. The moisture responsive element of claim 1, in which said salt is selected from the group consisting of sodium, lithium, ammonium, urea, triethylene-diamine, hexamethylene-tetramine and tetramethyl guanidine salt.

5. The moisture responsive element of claim 1, in which the moisture responsive organic membrane further comprises a water soluble non-crosslinked polymer.

6. The moisture responsive element of claim 5, in which the water soluble polymer is selected from the group consisting of polyvinyl alcohol and methyl cellulose.

7. The moisture responsive element of claim 1, in which the thickness of the protective layer is from 0.5 to 10 $\mu$m.

* * * * *